(12) United States Patent
Stradella et al.

(10) Patent No.: US 7,275,660 B2
(45) Date of Patent: Oct. 2, 2007

(54) DOSE INDICATOR FOR FLUID PRODUCT DISPENSING DEVICE

(75) Inventors: Fabio Stradella, Camogli (IT); Giuseppe Stradella, Camogli (IT)

(73) Assignee: Valois SAS, Neubourg (FR)

( * ) Notice: Subject to any disclaimer, the term of this patent is extended or adjusted under 35 U.S.C. 154(b) by 430 days.

(21) Appl. No.: 10/523,213

(22) PCT Filed: Jul. 15, 2003

(86) PCT No.: PCT/FR03/02233

§ 371 (c)(1),
(2), (4) Date: Jan. 27, 2005

(87) PCT Pub. No.: WO2004/013582

PCT Pub. Date: Feb. 12, 2004

(65) Prior Publication Data

US 2006/0163275 A1      Jul. 27, 2006

(30) Foreign Application Priority Data

Jul. 29, 2002  (FR) .................................. 02 09617

(51) Int. Cl.
*B67D 5/22*   (2006.01)
(52) U.S. Cl. ..................... 222/36; 128/205.23; 215/230
(58) Field of Classification Search ................. 222/36, 222/30, 32, 22; 128/205.23, 200.23, 200.14, 128/200.18, 200.24; 116/306, 309; 215/230
See application file for complete search history.

(56) References Cited

U.S. PATENT DOCUMENTS

| 5,421,482 | A | | 6/1995 | Garby et al. |
| 5,482,030 | A | * | 1/1996 | Klein ..................... 128/200.23 |
| 6,082,358 | A | * | 7/2000 | Scarrott et al. ......... 128/205.23 |
| 6,679,251 | B1 | * | 1/2004 | Gallem et al. .......... 128/200.23 |
| 6,769,601 | B2 | * | 8/2004 | Haikarainen et al. ..... 235/87 R |
| 6,997,349 | B2 | * | 2/2006 | Blacker et al. ................ 222/23 |
| 7,191,918 | B2 | * | 3/2007 | Ouyang et al. ................ 222/36 |
| 7,195,134 | B2 | * | 3/2007 | Ouyang et al. ................ 222/36 |

FOREIGN PATENT DOCUMENTS

EP          0 254391 A       1/1988

* cited by examiner

*Primary Examiner*—Lien M. Ngo
(74) *Attorney, Agent, or Firm*—Sughrue Mion Pllc.

(57) ABSTRACT

The present invention relates to a dose indicator (A) for a fluid dispenser device (B), the indicator indicating the number of doses dispensed or the number of doses still to be dispensed. The indicator is particularly adapted to aerosols including metering valves, and presents dimensions that are very small and independent of the number of doses to be indicated.

15 Claims, 4 Drawing Sheets

DOSE INDICATOR FOR FLUID PRODUCT DISPENSING DEVICE

The present invention relates to a dose indicator, and to a fluid dispenser device including such an indicator.

In the field of fluid dispenser devices for dispensing several doses, and in particular in the field of sprays, numerous systems have been developed for indicating the number of doses dispensed or the number of doses still to be dispensed.

Most of those systems present numerous drawbacks. Thus, they are generally based on a plurality of toothed wheels forming gears, with the number of wheels depending on the quantity of doses to be counted. Consequently, the counters or indicators can become very complex, bulky, and therefore costly to manufacture and to assemble. In addition, numerals are generally used as indicators, and are often difficult for the user to read, in particular when the dispenser devices are designed to dispense a large number of doses, e.g. up to 200 doses. Furthermore, all current dose counter or indicator systems are unsuitable for use by the visually impaired, and in particular by the blind. Another major drawback resides in the fact that existing counters generally need an assembly procedure for assembling the dispenser device that is modified by the presence of the counter, and that therefore differs from the normal assembly procedure. This increases the complexity of the device, and consequently implies a higher cost.

In addition, most dose indicator systems are disposed on the axial end of the reservoir, perpendicular to the axis of displacement of the reservoir during actuation, thereby implying that the system is assembled after the reservoir has been put in place. This increases the complexity of assembly, and therefore increases its cost. Document U.S. Pat. No. 5,421,482 discloses such an indicator system.

An object of the present invention is to provide a dose indicator that is intended for a fluid dispenser device, and that does not have the above-mentioned drawbacks.

In particular, an object of the present invention is to provide a dose indicator which is simple and inexpensive to manufacture and to assemble, and which can, in particular, be applied to all existing fluid dispenser devices without implying a modification to the assembly procedure.

Another object of the present invention is to provide a dose indicator which is small, regardless of the number of doses contained in the dispenser device.

Another object of the present invention is to provide a dose indicator which forms a complete and separate unit, and which includes, in particular, the actuator means for actuating the indicator.

Another object of the present invention is to provide a dose indicator which can be read easily by the user, and which can also be used by the visually impaired, and in particular by the blind.

Another object of the present invention is to provide a dose indicator which can be assembled before the reservoir is put in place.

Another object of the present invention is to provide a dose indicator which is not disposed on an axial end of the reservoir.

The present invention therefore provides a dose indicator for a fluid dispenser device, said indicator including a rotary element that is displaceable in rotation, and a slide member that is displaceable in translation, said rotary element including a profile co-operating with a projection of said slide member, so that each rotation of said rotary element causes said slide member to be displaced in translation, the position of said slide member indicating the number of doses dispensed or the number of doses still to be dispensed, said rotary element being a thin disk including a set of teeth, said set of teeth co-operating with actuator means designed to cause said rotary disk to turn, said indicator being characterized in that said actuator means include a drive element secured to a ring surrounding said set of teeth, said drive element coming into co-operation with said set of teeth each time a dose is dispensed.

Advantageously, said profile is a spiral-shaped profile.

Advantageously, said rotary element and said slide member are disposed in a cover including a display window.

Advantageously, the rotary element, the slide member, the actuator means, and the cover form a unit which can be assembled in a fluid dispenser device.

Advantageously, said slide member slides in guide means, such as ribs, provided in said cover.

Advantageously, said ring includes anti-return means preventing said rotary disk from turning in the direction opposite to the direction in which it is turned by said drive element.

Advantageously, said actuator means include at least one flexible tab.

Advantageously, said actuator means include a transmission element which is designed to co-operate with said fluid dispenser device each time said device is actuated, said transmission element also co-operating with said drive element so as to cause said rotary disk to turn.

Advantageously, said transmission element is a shoulder secured to said drive element, and co-operating with a portion of the fluid dispenser device which moves during actuation.

Advantageously, said slide member comprises a thin plate provided on one side with indicator means, and on the other side with said projection, said indicator means co-operating with a display window so that said indicator means are visible and/or can be touched by the user.

Advantageously, said indicator means are visual and/or tactile.

Advantageously, said visual indicator means include portions of different colors, a displacement in translation of said thin plate modifying the distribution of said colors in said display window.

Advantageously, said tactile indicator means include projecting portions co-operating with projections provided around said window, thereby enabling the positions of said moving projecting portions to be located relative to said fixed projections by touch.

The present invention also provides a fluid dispenser device, comprising a fluid reservoir and a dispenser member, such as a pump or a valve, mounted on said reservoir, and further comprising a dose indicator as defined above.

Advantageously, the dose indicator is actuated by a portion of the reservoir which is displaced while the device is being actuated, and which co-operates with a transmission element of said indicator.

Other characteristics and advantages of the present invention appear more clearly from the following detailed description of a particular embodiment thereof, given by way of non-limiting example, and with reference to the accompanying drawings, and in which.

The dose indicator A of the present invention applies to any type of fluid dispenser device. However, it applies more particularly to a spray, and advantageously to an aerosol, including a metering valve mounted on a receptacle containing a fluid for dispensing and a propellant gas.

Figure 1:
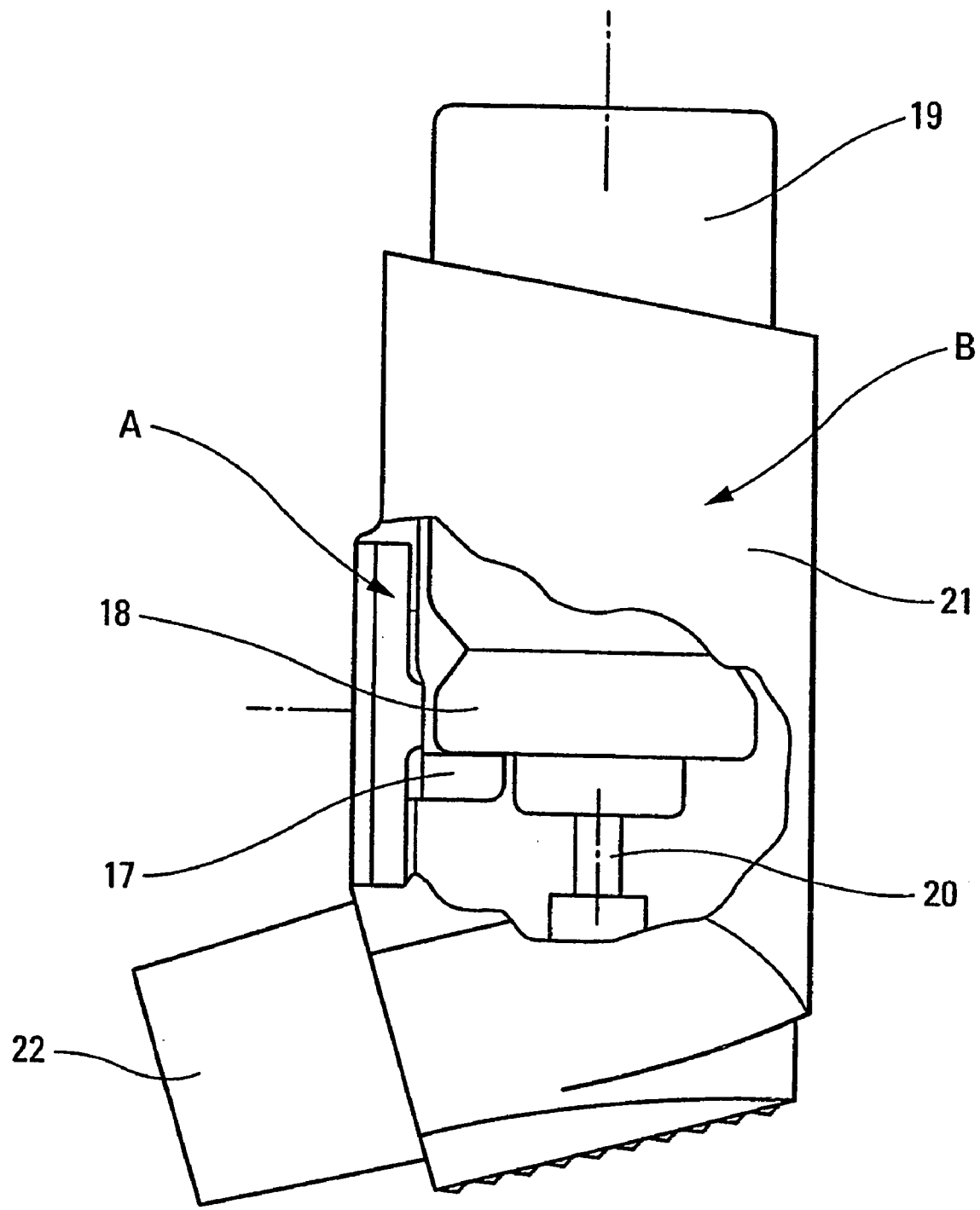
FIG. 1 is a partially cut-away diagrammatic side view of a fluid dispenser device including a dose indicator constituting an advantageous embodiment of the present invention.
Figure 2:
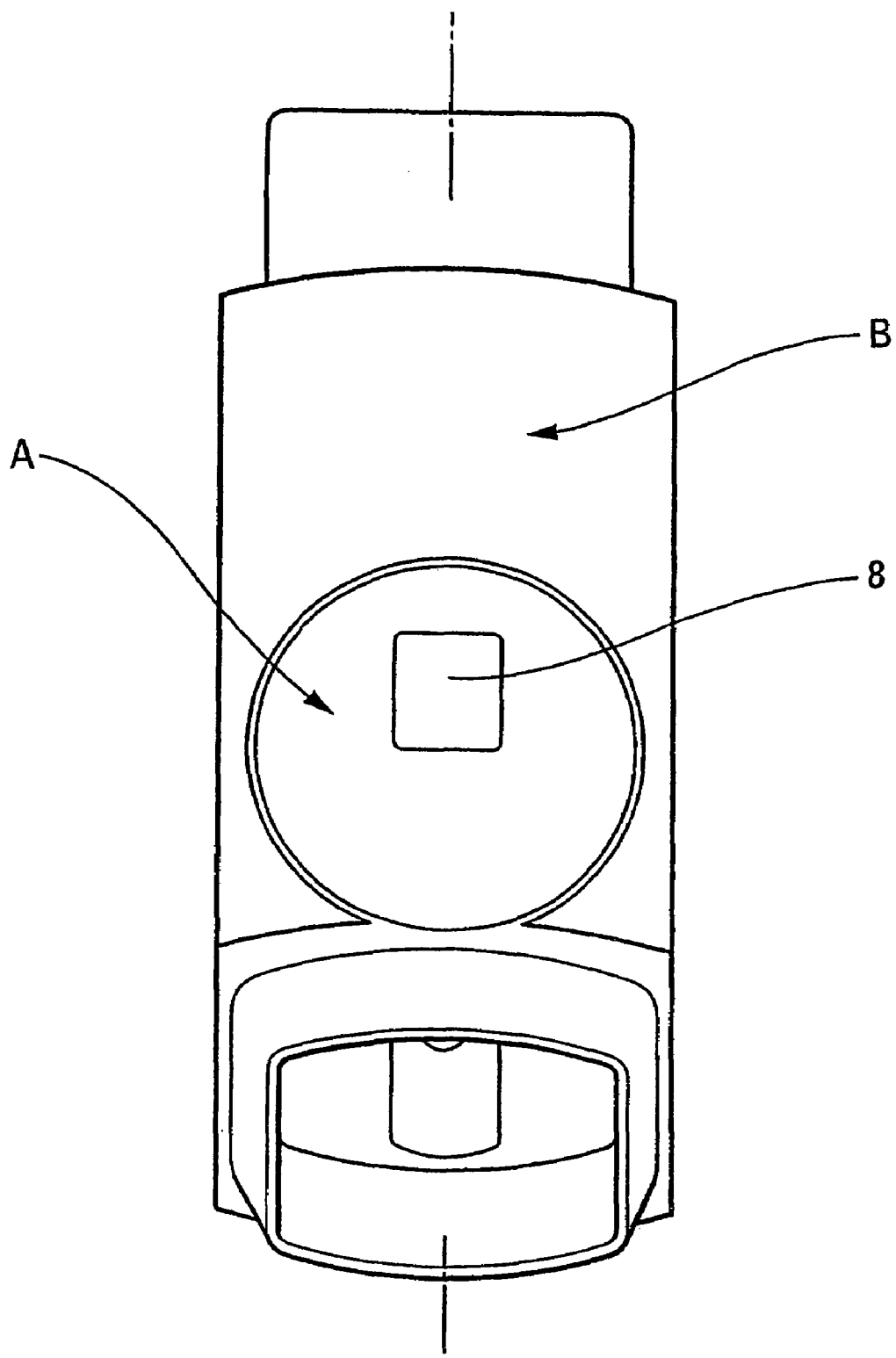
FIG. 2 is a front view similar to the FIG. 1 view.
Figure 3:
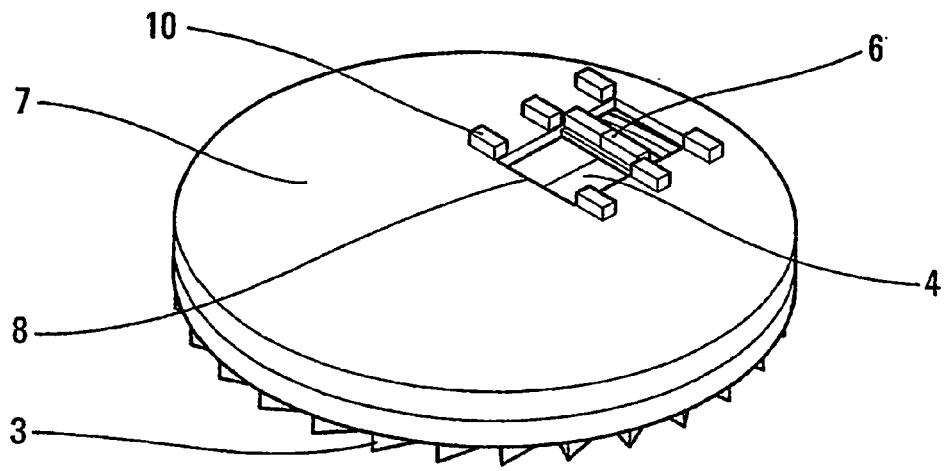
FIG. 3 is a diagrammatic perspective view of a portion of a dose indicator constituting an advantageous embodiment of the present invention.
Figure 4:
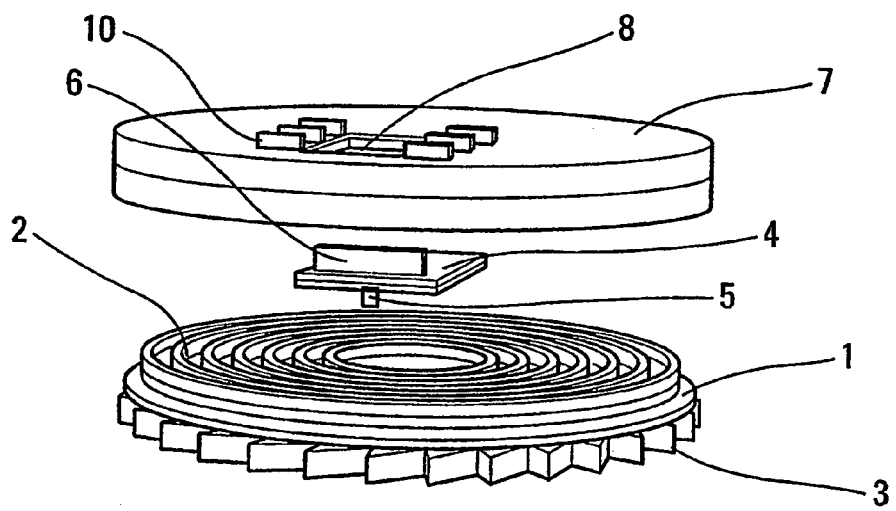
FIG. 4 is an exploded view of a portion of a dose indicator constituting an advantageous embodiment of the invention.
Figure 5:
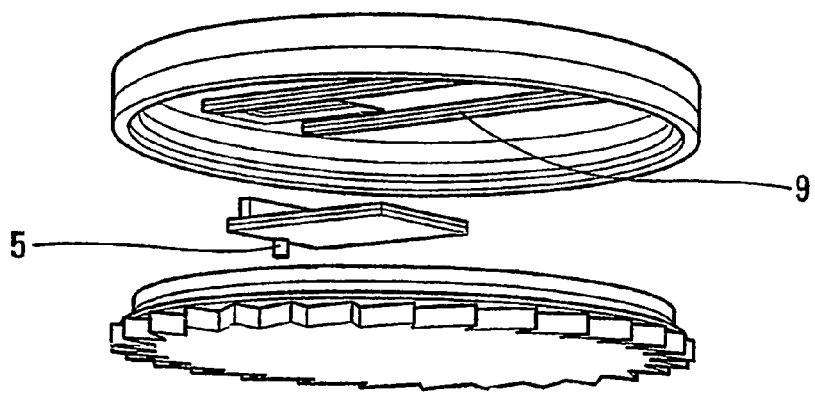
FIG. 5 is a view similar to the FIG. 4 view, seen from a different angle.

FIGS. 1 and 2 diagrammatically show a dispenser device B to which the dose indicator A of the present invention is particularly adapted. The device comprises a body 21 and a reservoir 19 on which a metering valve 20 is assembled, the device B being actuated by axial displacement of the reservoir 19 inside the body 21, said displacement causing the rod of the valve 20 to be compressed, thereby causing a dose of substance to be expelled through the mouthpiece 22. Naturally, the present invention also applies to other types of dispenser device, and in particular to spray devices of the nasal type, or to devices including a pump instead of the valve.

FIGS. 3 to 6 show, more particularly, an embodiment of the dose indicator A, which can, in particular, be used with a fluid dispenser device B as described above. The dose indicator comprises a rotary element 1 made in the form of a rotary disk, and designed to rotate about an axis of rotation that is substantially perpendicular to said disk 1. The rotary disk 1 is thin, and is provided with a profile, preferably a spiral-shaped profile 2, which can advantageously be formed by means of a rib. The disk 1 further comprises a set of teeth 3 provided on its periphery, said set of teeth being designed to co-operate with actuator means which are designed to cause said disk 1 to turn, and which are described in greater detail below.

The indicator A shown in the figures further comprises a slide member 4 designed to be displaced in translation. The slide member 4 includes a projection 5, or any other equivalent means, which co-operates with said spiral-shaped profile 2 of the rotary disk 1. In particular, a turn of the rotary disk 1 causes the projection 5 to be displaced inside the spiral-shaped profile 2, thereby causing the slide member 4 to be displaced in translation. The slide member 4 is preferably made in the form of a thin plate, which carries indicator means 6 on one side, and on the other side carries said projection 5 co-operating with the rotary disk 1.

The rotary element 1 and the slide member 4 are advantageously disposed in a cover 7 which is preferably also thin in structure, and which includes a display window 8 with which the indicator means 6 of the slide member 4 co-operate so as to be visible, or so as to enable them to be touched by a user.

The indicator means 6 can be visual and/or tactile. Visual indicator means can include portions of different colors so that a displacement in translation of said thin plate 4 in said window 8 causes a different distribution of said colors to appear in said window. The user can thus see the number of doses that remain to be dispensed, or the number of doses that have already been dispensed, as a function of the distribution of the colors in said window. Either the slide member 4 is itself provided with portions of different colors, e.g. green and red, or the slide plate 4 has a defined color, and the rotary disk 1 disposed therebeneath has a different color, so that as the plate 4 is displaced in translation in the window 8, the different colored rotary disk 1 progressively appears in said window, enabling the user to visualize progress in dispensing doses. Advantageously, the invention also provides tactile indicator means which can include projecting portions 6 provided on the slide member 4, and projections 10 which can be provided around said display window 8, e.g. by being integrated in the cover 7. By means of touch, the user can thus locate the positions of said moving projecting portions 6 of the slide member 4 relative to said fixed projections 10 of said lid 7. This embodiment makes it possible for a visually impaired person, and in particular a blind person, to know the position of the dose indicator, and therefore know the approximate number of doses that remain to be dispensed, or that have already been dispensed. Naturally, the tactile and/or visual indicator means can be made in some other way, the above descriptions being given merely by way of non-limiting example.

The indicator A, and in particular the rotary disk 1, can advantageously be actuated by actuator means integrated in said indicator A. Thus, with reference to FIGS. 3 to 6, the actuator means include a drive element 11 secured to a ring 12 which surrounds said set of teeth 3 of the rotary disk 1. The drive element 11 is designed to co-operate with said set of teeth 3 each time a dose is dispensed. Anti-return means 13 are advantageously provided, in particular in said ring 12, to prevent said rotary disk 1 from turning in the direction opposite to the direction in which it is turned by the drive element 11 during actuation.

The actuator means also advantageously include a transmission element 17 which is designed to co-operate with the fluid dispenser device B on each actuation, said transmission element 17 also co-operating with said drive element 11 so as to cause said rotary disk 1 to turn. In particular, and as shown in particular in FIG. 1, said transmission element 17 is a shoulder that is secured to the drive element 11, and that co-operates with a portion 18 of the fluid dispenser device B which moves during actuation. In the example shown, said portion 18 is the fixing ring for fixing the metering valve 20 onto the reservoir 19. Naturally, and more generally, any portion which is displaced while the device B is being actuated, is suitable for co-operating with the shoulder 17 so as to actuate the dose indicator A.

Figure 6:
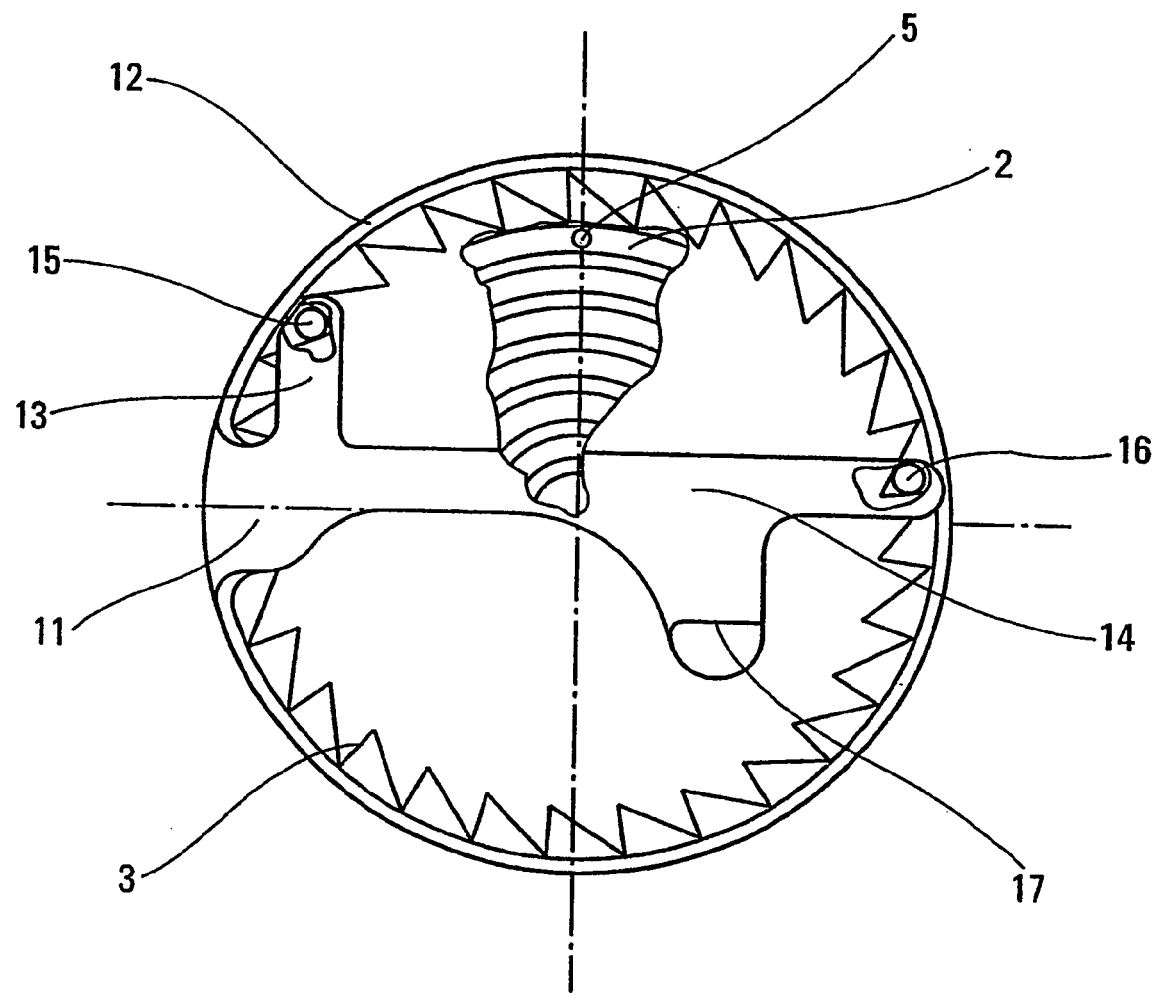
FIG. 6 is a partially cut-away diagrammatic section view of a portion of the indicator of FIGS. 3 to 5.

With reference to FIG. 6, the actuator means can include a flexible tab 11 forming the drive element, said flexible tab 11 can be provided with two flexible portions 13 and 14, each supporting a pin 15 and 16 having a bottom that is shaped in the form of an inclined plane. The flexible tab 11 also supports said shoulder 17, and when the spray device B is actuated, the fixing ring 18 of the reservoir causes the flexible portion 14 of the arm 11 to bend parallel to the rotary disk 1, thereby causing said disk to turn by drive from the pin 16 which co-operates with the set of teeth 3. Simultaneously, the flexible portion 13 is forced to flex perpendicularly to the rotary disk 1 by the action of the set of teeth 3 against the inclined bottom of the pin 15. When the reservoir 19 returns to its rest position, the flexible portion 14 is unloaded, and can consequently flex perpendicularly to the rotary disk 1 under drive from the pin 16 against the set of teeth 3. In this way, the pin 16 becomes engaged with the next tooth in the set of teeth 3, and the device is ready for the next actuation. Obviously, each incremental turn of the rotary disk 1 causes the slide member 4 to move in translation via its projection 5 which co-operates with the spiral-shaped profile 2 of the rotary disk 1.

The cover 7 advantageously includes guide means 9, such as rails or ribs, which co-operate with the slide member 4 so as to guide it in its displacement in translation.

The number of teeth on the set of teeth 3 and the number of turns in the spiral-shaped profile 2 of the rotary disk 1 therefore give the characteristics of the dose indicator, and in particular, the number of doses that the indicator can count. Thus, in the example shown in FIG. 6, the set of teeth 3 has thirty teeth, and the spiral-shaped profile 2 has seven turns. Consequently, the dose indicator A shown in the drawings is designed to count about 210 doses. Naturally, this number can be varied as required by modifying the structure of the spiral-shaped profile 2 or by modifying the number of teeth in the set of teeth 3. The present invention therefore makes it possible to produce dose indicators that are designed to count any number of doses without modifying the shape or the size of said indicator. As mentioned above, the structure of the present indicator is particularly small, in particular in terms of thickness, and the indicator A can therefore be integrated very easily into existing fluid dispenser devices B, as shown in FIGS. 1 and 2.

In a variant, the spiral-shaped profile 2 of the rotary disk 1 could include a terminal portion having a modified profile. The terminal portion of the spiral is the portion which co-operates with the projection 5 of the slide member 4 when the last dose is counted. The modified profile could be a modification to the curvature of the spiral, or could even be a rectilinear portion, having the effect of modifying the displacement in translation of the slide member 4, and in particular having the effect of accelerating it or of moving it farther. Thus, the user is informed that the last dose has been dispensed and that the device is empty.

The dose indicator of the present invention makes it possible, in simple and therefore inexpensive manner, to display the number of doses dispensed or the number of doses still to be dispensed from the device. The structure of the indicator is very thin, regardless of the number of doses that it needs to indicate, and it does not include any projecting portion that implies modifications need to be made to the device to which it is applied. As shown in FIG. 1, the dose indicator A of the present invention is applied very easily to any existing device, without said devices needing to be modified. The presence of the indicator A also does not require the assembly process for assembling the device B to be modified. In particular, the indicator can be assembled before the reservoir is put in place. By way of example, the indicator can be put in place in the device B via an opening provided for this purpose on the front portion of the body 21 of the device. Another advantage of the indicator of the present invention is that the actuator means of the indicator are integrated therein, so that the indicator forms an autonomous and separate unit which can be pre-assembled and can easily be integrated into any fluid dispenser device, in particular before assembling the reservoir. As also explained above, the indicator of the present invention can be used by the blind or by the visually impaired, and the combined visual and tactile indication guarantees, for all users, reliable information about the number of doses dispensed or about the number of doses still to be dispensed.

Naturally, the present invention is described above with reference to a particular embodiment thereof shown in the drawings, but it is not in any way limited to that particular embodiment. On the contrary, any modifications could be applied thereto by a person skilled in the art, without going beyond the ambit of the present invention as defined by the accompanying claims.

The invention claimed is:

1. A dose indicator (A) for a fluid dispenser device (B), said indicator including a rotary element (1) that is displaceable in rotation, and a slide member (4) that is displaceable in translation, said rotary element (1) including a profile (2) co-operating with a projection (5) of said slide member (4), so that each rotation of said rotary element (1) causes said slide member (4) to be displaced in translation, the position of said slide member (4) indicating the number of doses dispensed or the number of doses still to be dispensed, said rotary element (1) being a thin disk including a set of teeth (3), said set of teeth (3) co-operating with actuator means (11, 17) designed to cause said rotary disk (1) to turn, said indicator being characterized in that said actuator means include a drive element (11) secured to a ring (12) surrounding said set of teeth (3), said drive element (11) coming into co-operation with said set of teeth (3) each time a dose is dispensed.

2. An indicator according to claim 1, in which said profile (2) is a spiral-shaped profile.

3. An indicator according to claim 1, in which said rotary element (1) and said slide member (4) are disposed in a cover (7) including a display window (8).

4. An indicator according to claim 3, in which the rotary element (1), the slide member (4), the actuator means (11, 17), and the cover (7) form a unit which can be assembled in a fluid dispenser device (B).

5. An indicator according to claim 3, in which said slide member (4) slides in guide means (9), such as ribs, provided in said cover (7).

6. An indicator according to claim 1, in which said ring (12) includes anti-return means (13) preventing said rotary disk (1) from turning in the direction opposite to the direction in which it is turned by said drive element (11).

7. An indicator according to claim 1, in which said actuator means include at least one flexible tab (11).

8. An indicator according to claim 1, in which said actuator means include a transmission element (17) which is designed to co-operate with said fluid dispenser device (B) each time said device is actuated, said transmission element (17) also co-operating with said drive element (11) so as to cause said rotary disk (1) to turn.

9. An indicator according to claim 8, in which said transmission element (17) is a shoulder secured to said drive element (11), and co-operating with a portion (18) of the fluid dispenser device (B) which moves during actuation.

10. An indicator according to claim 1, in which said slide member (4) comprises a thin plate provided on one side with indicator means (6), and on the other side with said projection (5), said indicator means (6) co-operating with a display window (8) so that said indicator means are visible and/or can be touched by the user.

11. An indicator according to claim 10, in which said indicator means (6) are visual and/or tactile.

12. An indicator according to claim 11, in which said visual indicator means include portions of different colors, a displacement in translation of said thin plate (4) modifying the distribution of said colors in said display window (8).

13. An indicator according to claim 11, in which said tactile indicator means include projecting portions (6) co-operating with projections (10) provided around said window (8), thereby enabling the positions of said moving projecting portions to be located relative to said fixed projections (10) by touch.

14. A fluid dispenser device (B), comprising a fluid reservoir (19) and a dispenser member, such as a pump or a valve, mounted on said reservoir (19), said device being characterized in that it further comprises a dose indicator (A) according to claim 1.

15. A device according to claim 14, in which the dose indicator (A) is actuated by a portion (18) of the reservoir (19) which is displaced while the device (B) is being actuated, and which co-operates with a transmission element (17) of said indicator (A).

* * * * *